United States Patent [19]

Baisden

[11] 4,337,245
[45] Jun. 29, 1982

[54] NUTRIENT COMPOUND

[76] Inventor: C. Robert Baisden, 3227 Ramsgate Rd., Augusta, Ga. 30909

[21] Appl. No.: 302,313

[22] Filed: Sep. 14, 1981

Related U.S. Application Data

[63] Continuation-in-part of Ser. No. 170,432, Jul. 21, 1980, abandoned.

[51] Int. Cl.$^3$ .................... A61K 33/26; A61K 33/30; A61K 33/32; A61K 33/34
[52] U.S. Cl. ................................ 424/131; 424/140; 424/144; 424/145; 424/147
[58] Field of Search ............... 424/140, 131, 176, 144, 424/145, 147

[56] References Cited

U.S. PATENT DOCUMENTS

| | | | |
|---|---|---|---|
| 2,034,783 | 3/1936 | Torigan | 424/140 |
| 2,798,023 | 7/1957 | Berger | 424/131 |
| 2,816,854 | 12/1957 | Cross | 424/131 |
| 3,275,514 | 9/1966 | Sollman et al. | 424/176 |
| 3,712,291 | 1/1973 | Freeman | 424/331 |

Primary Examiner—Stanley J. Friedman
Attorney, Agent, or Firm—Morton J. Rosenberg

[57] ABSTRACT

A nutrient compound formed of a plurality of elements having predetermined weight ratio percentages each to the other. The nutrient compound is synthesized in accordance with the particular elements being found in the Earth's crust. The elements utilized in the nutrient compound include Scandium, Titanium, Vanadium, Chromium, Manganese, Iron, Cobalt, Nickel, Copper, and Zinc, which correspond to the upper elements in Groups IIIB, IVB, VB, VIB, VIIB, VIII, IB, and IIB of the Periodic Table. The nutrient compound utilizes the elements in the same approximate weight ratio found in the Earth's crust. The elements displace lower elements in each of the Groups of the Periodic Table within organic life forms in order to achieve a bio-chemical ratio more in concert with the manner in which such organic life has evolved.

11 Claims, No Drawings

NUTRIENT COMPOUND

REFERENCE TO RELATED APPLICATIONS

This Patent Application is a Continuation-in-Part of U.S. Patent Application Ser. No. 170,432, filed July 21, 1980, now abandoned.

BACKGROUND OF THE INVENTION

1. Field of the Invention

This invention pertains to nutrient compounds for ingestion by mammals and/or plant life. This invention relates to a nutrient compound including a predetermined number of elements combined in an approximate weight percentage ratio, each to the other in accordance with the weight percentage ratio found in the Earth's crust. Still further, this invention relates to a nutrient compound which utilizes predetermined elements for displacing other more toxic elements found in the environment and being ingested by mammals and plant life. More in particular, this invention relates to a nutrient compound which includes particular elements from Groups IIIB, IVB, VB, VIB, VIIB, VIII, IB, and IIB of the Periodic Table. More in particular, this invention relates to the use of the elements Scandium, Titanium, Vanadium, Chromium, Manganese, Iron, Cobalt, Nickel, Copper, and Zinc, in predetermined weight proportions each to the other to provide a nutritional compound for ingestion by mammals and plant life. More in particular, this invention is directed to providing a nutrient compound which optimizes the chemical evolutionary process of animal and plant life. Additionally, the subject nutrient compound is directed to a nutrient compound in solution which may be ingested by mammals and plant life, to provide a balance of elements found in the Earth's crust from which such life has evolved.

Still further, the nutrient compound of the subject concept is directed to a two-fold purpose, (1) the provision of trace elements necessary to organic life, wherein such trace elements include Scandium, Titanium, Vanadium, Chromium, Manganese, Iron, Cobalt, Nickel, Copper, and Zinc; and, (2) the use of the aforementioned trace elements to drive out other more toxic elements contained within organic systems.

2. Prior Art

Nutritional compounds utilizing specific elements for ingestion into mammals or plant life are well-known in the art. However, it is not believed that the particular weight percentage ratio of each of the elements as provided in the subject invention concept in accordance with those percentages found in the Earth's crust has been found in the prior art. The best prior art known to Applicant includes U.S. Pat. Nos. 3,275,514; 2,943,100; 2,034,783; 1,812,560; 2,816,854; 2,798,023; 3,215,626; 3,712,291; 2,028,575; 4,070,488; 3,832,457; 3,734,742; 3,803,308; 3,923,982; 1,649,269; and 2,885,393. These references include various percentages of elements to be either ingested within mammals or utilized for agricultural products. However, it is not believed that any of the references shown provide for the predetermined weight percentages of the specific elements as is provided in the Earth's crust for use as a nutritional compound.

In some of the prior art, specific elements are incorporated for use in mammal or plant life processes. However, such prior art does not appear to direct itself to the concept that particular elements in Groups IIIB, IVB, VB, VIB, VIIB, VIII, IB, AND IIB have the ability of displacing other unwanted elements from the mammalian body.

Additionally, such prior art does not appear to address itself to the combination and percentages of specific elements found in the Earth's crust. Thus, such prior art does not show an optimum chemistry evolution directed to the mammalian life form and/or plant life.

It is well-known in the prior art that human beings may suffer from deficiencies of various trace elements. Specific trace elements are now commercially available and may be purchased where a trace element is diagnosed. However, such prior compounds do not provide for trace element percentages in accordance with that found in the Earth's crust, as is necessary to the inventive concept of the subject invention. Still further, such prior compounds do not provide for the insert of trace elements at the top of the Periodic Chart for use in driving out other more toxic elements in each Group of the Periodic Table, as is necessary to the subject concept as defined herein.

Prior art compounds which do include trace elements are not believed to provide for the two-fold purpose of insert of such trace elements to the human body in the percentages as detailed in this overall concept. Thus, where only one trace element is provided in such prior art compounds, such would not necessarily be at the top of the Periodic Chart in a particular chemical group, and would thus not drive out or eliminate other toxic elements lower in that particular chemical grouping.

SUMMARY OF THE INVENTION

A nutrient compound having a predetermined plurality of elements being combined in an approximate weight percentage ratio each to the total of the elements contained within the nutrient compound. The elements included are within the approximate weight percentage ratio ranges of: (a) 0.032%–0.035% Scandium; (b) 11.090%–12.623% Titanium; (c) 0.247%–0.250% Vanadium; (d) 0.121%–0.141% Chromium; (e) 1.468%–1.689% Manganese; (f) 85.134%–86.455% Iron; (g) 0.030%–0.041% Cobalt; (h) 0.093%–0.106% Nickel; (i) 0.081%–0.085% Copper; and, (j) 0.120%–0.159% Zinc.

DESCRIPTION OF THE PREFERRED EMBODIMENTS

Referring now to the invention, there is provided a nutrient compound adapted for use in mammalians and plant life. It is the overall concept of the subject invention to provide predetermined elements in an overall compound which aids in eliminating or otherwise driving out other unwanted elements within the mammalian body or other organic systems to which the predetermined elements are inserted. Organic life has evolved in a manner such that it has been exposed to ratios or concentrations of basic elements in the Earth's crust over the evolutionary time domain and that the organic chemistry has thus adapted to these concentrations.

The subject nutrient compound has been formed into an aqueous solution and used for both ingestion in human beings and has further been used on plant life. The aqueous solution formed in accordance with specific examples hereinafter detailed in this Specification, has been used as a supplemental drink wherein one eight-ounce glass of liquid has been ingested each day for a period of months. Additionally, the aqueous solution has been used in connection with plant life and has been used as a watering agent into the soil around various plants. Obviously, this aqueous solution is inserted into the soil around the plants, the ratio of trace elements which is substantially the same as that found in the Earth's crust during evolution of the planet. The plant life has flourished and such nutrient compound has been found beneficial to the plant life growth. Further, as will be seen in further following experimental examples, the use of such nutrient compound in an aqueous solution has been shown to drive out specific elements lower in the Periodic Table for particular groupings, wherein such elements may be found at toxic levels in the subjects.

The nutrient compound of the subject invention may be formed into an aqueous solution as will be described in following paragraphs. However, it is to be understood that the nutrient compound as herein detailed may be utilized in solid or liquid form. The important consideration being that the nutrient compound contain specific elements having a predetermined concentration ratio each to the other in the approximate ratios found in the Earth's crust.

In the present ambient environment, organic life is exposed and ingests numerous toxic elements, and in particular, exposure to Platinum, Gold, Silver, Catalytic Elements, Cadmium, and other toxins has caused a high level of such toxins to be ingested within the organic life. The high concentration insert of such toxic elements has increased over the recent past, due to industrialization and other sociologic factors. The basic problem is that organic life often has ingested sufficient quantities of such toxic elements so as to cause an imbalance when taken with respect to the ratio and concentration of elements in the Earth's crust from which such organic life has evolved.

It will be noted on the Periodic Table that elements which are very low in concentration in the Earth's crust, but are at or near the top of the Periodic Table, such as Lithium, Boron, and Beryllium are extremely active elements. Such elements have extremely low concentrations in the Earth's crust and are toxic to organic life, except in infinitesimal amounts.

In opposition, elements such as Platinum and Mercury are also low in concentration in the Earth's crust, but are at a lower level on the Periodic Table, are extremely soluble in compounds, and are toxic to organic life in appreciable amounts. The low concentrations in the Earth's crust of such elements did not provide organic life with evolutionary characteristics to develop a chemistry in order to displace or otherwise utilize such elements, since the organic life was exposed to low concentrations of such. Due to the changing environment, as caused by advancing civilization, toxic elements substantially external to the range of such elements being found in the Earth's crust is being ingested into organic life at an increasing rate.

It is thus of major importance to the inventive concept of the subject Patent Application to provide a compound where essentially protective elements in substantially the same ratio in which such are found in the Earth's crust are provided for ingestion.

In particular, the nutrient composition of the subject Patent Application deals with those elements found in the Periodic Table associated with Groups: IIIB, IVB, VB, VIB, VIIB, VIII: IB, AND IIB. Still further, the composition as provided, utilizes the elements at the top of each of these Groups in the proportions generally found in the Earth's crust to drive out elements at a lower level in such Groups.

Thus, Group IIIB utilizes Scandium to displace Yttrium; Lanthanum; and, Actinum. Titanium found in Group IVB is used to displace Zirconium; Hafnium; and Rutherfordium. Vanadium found in Group VB is utilized for displacement of Technetium and Rhenium.

The three highest elements found in Group VIII, namely, Iron, Cobalt, and Nickel, are utilized respectively with Ruthenium, Osmium, and Rhodium, Iridium, and Palladium and Platinum. Copper found in Group IB is utilized for displacement of Silver and Gold. Zinc found in Group IIB is provided for displacement of Cadmium and Mercury. The particular use of Zinc to displace Mercury from organic bodies is clearly shown in an experiment hereinafter provided in this Specification.

Thus, the elements Scandium, Titanium, Vanadium, Chromium, Manganese, Iron, Cobalt, Nickel, Copper, and Zinc, are utilized in relative ratios found in the Earth's crust to provide protection against those elements in the associated Groups in the Periodic Table now found to be increasing beyond the proportion acceptable to organic life.

The trace elements of Scandium, Titanium, Vanadium, Chromium, Manganese, Iron, Cobalt, Nickel, Copper, and Zinc are generally found in mammals and specifically in human beings in varying amounts. Deficiencies of such trace elements may account for a multiplicity of ailments.

Additionally, as has been previously stated in prior paragraphs, various elements found in the human body may accumulate to toxic levels. Thus, the nutrient compound of the subject concept uses the aforementioned specific elements to eliminate or drive out other elements from the body.

The compound of the subject concept thus has a two-fold purpose of (1) providing trace elements to the body; and, (2) using such trace elements to remove other toxic elements from the body.

The crustal abundance of elements has been catalogued in the McGraw-Hill Encyclopedia of Science and Technology where the elements Scandium through Zinc are catalogued in weight parts per million. These weight parts of each of the aforementioned elements are listed in Table I, shown below:

TABLE I

| ELEMENT | EARTH CRUSTAL ABUNDANCE (PPM) |
|---|---|
| Scandium (Sc) | 14.–22. |
| Titanium (Ti) | 4,400.–8,600. |
| Vanadium (Va) | 98.–170. |
| Chromium (Cr) | 48.–96. |
| Manganese (Mn) | 670.–1,000. |
| Iron (Fe) | 34,300.–58,000. |
| Cobalt (Co) | 12.–28. |
| Nickel (Ni) | 37.–72. |
| Copper (Cu) | 32.–58. |
| Zinc (Zn) | 63.–82. |

The weight percentage of each of the elements shown in Table I, when taken with respect to each other, is provided in Table II, shown below:

TABLE II

| ELEMENT | WEIGHT PERCENTAGE OF ELEMENTS WHEN TAKEN WITH RESPECT TO THE OTHERS |
|---|---|
| Scandium (Sc) | 0.03528–0.03229 |
| Titanium (Ti) | 11.09038–12.62329 |
| Vanadium (Va) | 0.24701–0.24953 |
| Chromium (Cr) | 0.12098–0.14091 |
| Manganese (Mn) | 1.68876–1.46782 |
| Iron (Fe) | 86.4546–85.13386 |
| Cobalt (Co) | 0.03024–0.04109 |
| Nickel (Ni) | 0.09326–0.10568 |
| Copper (Cu) | 0.08065–0.08513 |
| Zinc (Zn) | 0.15879–0.12036 |

It is thus the inventive concept of the subject invention to provide a chemical compound which includes the elements shown in Tables I and II being combined in an approximate weight percentage ratio, each to the total of the elements which includes: (a) 0.035%–0.032% Scandium; (b) 11.09%–12.62% Titanium; (c) 0.247%–0.249% Vanadium; (d) 0.121%–0.141% Chromium; (e) 1.689%–1.468% Manganese; (f) 86.455%–85.134% Iron; (g) 0.030%–0.041% Cobalt; (h) 0.093%–0.106% Nickel; (i) 0.081%–0.085% Copper; and, (j) 0.159%–0.120% Zinc.

In a preferred embodiment of the compound, such has a predetermined plurality of elements which are combined in the approximate weight percentage ratio of each to the other of the elements, which includes: (a) 0.033% Scandium; (b) 11.5% Titanium; (c) 0.247% Vanadium; (d) 0.13% Chromium; (e) 1.55% Manganese; (f) 85.5% Iron; (g) 0.035% Cobalt; (h) 0.095% Nickel; (i) 0.082% Copper; and, (j) 0.14% Zinc.

In an embodiment of the subject inventive composition, an aqueous solution containing the aforementioned concentrations and percentage of each of the elements has been synthesized. In one form, the compositions used in the compound included Scandium Chloride; Titanium Chloride; Ammonium Vanadate; Chromium Chloride; Manganese Chloride; Ferric Chloride; Cobalt Chloride; Nickel Chloride; Copper Chloride; and Zinc Chloride. The important consideration being that each of the elements were provided within the percentage ranges each to the other shown in Table II.

The compositions were diluted to one liter in a volumetric flask and by providing distilled water, such compounds were found to be soluble. Dilution was then provided in a further process step by diluting this concentrate by an order of magnitude to provide one part per billion of the aforementioned elements. This process step was accomplished by inserting distilled water in the appropriate amount and stirring to provide a final solution. The entire process steps were performed at room temperature at ambient pressure.

The final aqueous solution was found to have a pH of approximately 1.0–2.0. The pH was varied by adding Sodium Bi-carbonate to displace the pH value to approximately 7.0. The pH value was varied between 3.5–7.0 which was found to be an acceptable palatable range for the solution.

The final aqueous solution was then bottled and used as a drink to be ingested through the mouth. The final aqueous solution may be used as a supplemental drink to insure an adequate amount of trace elements within the human body, while aiding in the elimination of other elements which may achieve a high toxicity level percentage in the body.

Other aqueous solutions were prepared for insert into the soil around plant life. In such solutions, the pH range was left in the 1.0–2.0 range, since obviously palatability had no effect on the plant life. It was found that the plants which were watered by this final solution flourished during the growing period.

Numerous experiments were initiated to provide the nutrient compound of the subject invention. The overall concept in the experiments was to include predetermined weight percentages of each of the aforementioned elements when taken with respect to the total weight of each of the elements in the same proportions as that found in the Earth's crust. Thus, the weight percentages of each of the elements taken with respect to the other elements is to be provided in the final solution in the percentages shown in Table II. The elements, composition used containing the elements, particular element atomic weights and composition containing the element atomic weight, is shown in the following Table III:

| Element | Composition Used | Element Atomic Weight | Composition Molecular Weight |
|---|---|---|---|
| Scandium | ScCl$_3$ | 44.96 | 151.31 |
| Titanium | TiCl$_4$ | 47.90 | 402.18 |
| Vanadium | NH$_4$VO$_3$ | 50.94 | 116.98 |
| Chromium | CrCl$_3$ . 6H$_2$O | 52.00 | 266.45 |
| Manganese | MnCl$_2$ . 4H$_2$O | 54.94 | 197.91 |
| Iron | FeCl$_3$ . 6H$_2$O | 55.85 | 270.30 |
| Cobalt | CoCl$_2$ . 6H$_2$O | 58.93 | 237.93 |
| Nickel | NiCl$_2$ . 6H$_2$O | 58.71 | 237.71 |
| Copper | CuCl$_2$ . 2H$_2$O | 63.55 | 170.48 |
| Zinc | ZnO . HCl | 65.37 | 287.54 |

The composition weight in micrograms per 1.0 mililiters of aqueous solution is provided by multiplying the composition molecular weight shown in Table III multiplied by the concentration of the particular element in the Earth's crust which is varied in accordance with Table I. This multiplication is divided by the element atomic weight, as shown in Table III to finally provide the total composition weight in micrograms per 1.0 mililiters of aqueous solution. The formula is shown in the following Equation I:

$$W = \frac{C_{M.W.} \cdot C_{E.C.}}{E_{A.W.}} \quad (1)$$

where:

W = Total Composition Weight (micrograms per 1.0 mililiter of solution)

$C_{M.W.}$ = Composition Molecular Weight $C_{E.C.}$ = Concentration of Element in Earth's crust (weight parts/million)

$E_{A.W.}$ = Element Atomic Weight

The composition molecular weight divided by the element atomic weight is multiplied by the weight of the particular element in parts per million found in the Earth's crust. In all of the experiments described below, the aforementioned elements were used throughout the range found in Table I. The composition molecular weight divided by the element atomic weight utilized in the experiments is shown below in Table IV:

| Element | Composition Used | $\frac{C_{MW}}{E_{AW}}$ |
|---|---|---|
| Scandium | ScCl$_3$ | 3.3654 |
| Titanium | TiCl$_4$ | 8.3962 |
| Vanadium | NH$_4$VO$_3$ | 2.2964 |
| Chromium | CrCl$_3$ . 6H$_2$O | 5.1240 |
| Manganese | MnCl$_2$ . 4H$_2$O | 3.6023 |
| Iron | FeCl$_3$ . 6H$_2$O | 4.8397 |
| Cobalt | CoCl$_2$ . 6H$_2$O | 4.0375 |
| Nickel | NiCl$_2$ . 6H$_2$O | 4.0489 |
| Copper | CuCl$_2$ . 2H$_2$O | 2.6826 |
| Zinc | ZnO . HCl | 4.3987 |

EXPERIMENT I

The initial experiment was conducted utilizing the elements at the low end of the element concentrations in the Earth's crust as provided in Table I. The compositions utilized in this experiment are shown in Table IV. The micrograms of composition per 1.0 mililiters of final solution were calculated and are shown below in Table V:

| Element | $C_{EC}$ (ppm) | $\frac{C_{MW}}{E_{AW}}$ | Micrograms of Composition/1.0 Ml. of Solution |
|---|---|---|---|
| Scandium | 14. | 3.3654 | 47.12 |
| Titanium | 4,400 | 8.3962 | 36,943.3 |
| Vanadium | 98. | 2.2964 | 225.05 |
| Chromium | 48. | 5.1240 | 245.95 |
| Manganese | 670. | 3.6023 | 2,413.54 |
| Iron | 34,300 | 4.8397 | 166,001.71 |
| Cobalt | 12. | 4.0375 | 48.45 |
| Nickel | 37. | 4.0489 | 149.81 |
| Copper | 32. | 2.6826 | 85.84 |
| Zinc | 63. | 4.3987 | 277.12 |

In this experiment, the compositions including the elements of concern were formed into an aqueous solution by incorporation of distilled water. The stirring and mixing of the compositions used in the aqueous solution was performed at room temperature and approximately 1.0 atmospheres of pressure. The resulting aqueous solution was found to have a pH value approximating 4.0–5.0. The pH value was varied by adding Sodium Bicarbonate to move the pH Value to approximately 7.0.

EXPERIMENT II

Experiment II was provided in the same manner and utilizing the same process steps as hereinbefore described for Experiment I. The only portion of the Experiment which was varied was directed to the concentration of the elements of concern when taken with respect to that amount found in the Earth's crust. In this experiment, the element parts per million was utilized in the mid-range of each of the elements shown in Table I. The concentration and the final weight of composition per 1.0 mililiter of solution is shown in the following Table VI:

| Element | $C_{EC}$ (ppm) | $\frac{C_{MW}}{E_{AW}}$ | Micrograms of Composition/1.0 Ml. of Solution |
|---|---|---|---|
| Scandium | 18. | 3.3654 | 60.58 |
| Titanium | 6500. | 8.3962 | 54,575.3 |
| Vanadium | 134. | 2.2964 | 307.72 |
| Chromium | 72. | 5.1240 | 368.93 |
| Manganese | 835. | 3.6023 | 3,007.92 |
| Iron | 46,150. | 4.8397 | 223,352.15 |
| Cobalt | 20. | 4.0375 | 80.75 |
| Nickel | 54.5 | 4.0489 | 220.67 |
| Copper | 45. | 2.6826 | 120.72 |
| Zinc | 72.5 | 4.3987 | 318.91 |

The resulting solution was varied in its pH value between 3.5–7.0 by the addition of Sodium Bicarbonate. This experiment composition was found to be more palatable to the taste than those compositions tried in Experiments I and III.

EXPERIMENT III

The final set of experiments were conducted with the aforementioned elements in a concentration as provided by the upper range of the elements in parts per million found in the Earth's crust as shown in Table I. The process steps were identical to that as hereinbefore shown and described for Experiments I and II. The concentrations and final weight compositions per one mililiter of solution as detailed in this Experiment, are provided in the following Table VII:

| Element | $C_{EC}$ (ppm) | $\frac{C_{MW}}{E_{AW}}$ | Micrograms of Composition/1.0 Ml. of Solution |
|---|---|---|---|
| Scandium | 22. | 3.3654 | 74.04 |
| Titanium | 8,600. | 8.3962 | 72,207.3 |
| Vanadium | 170. | 2.2964 | 390.39 |
| Chromium | 96. | 5.1240 | 491.90 |
| Manganese | 1,000. | 3.6023 | 3,602.3 |
| Iron | 58,000. | 4.8397 | 280,702.6 |
| Cobalt | 28. | 4.0375 | 113.05 |
| Nickel | 72. | 4.0489 | 291.52 |
| Copper | 58. | 2.6826 | 155.59 |
| Zinc | 82. | 4.3987 | 360.69 |

The final aqueous solution was found to have a pH value within the approximate range of 1.0–2.0. Once again, the pH was varied over a wide range by adding Sodium Bicarbonate.

In order to more specifically show the concept of the use of trace elements to drive out or eliminate other elements lower in the Periodic Table, it was decided to provide a series of experiments wherein Zinc is used to drive out Mercury. In order to achieve this experiment base, four treatment groups of Sprague-Daweley rats were used. Group I was a controlled group of rats wherein only distilled water was used for ingestion throughout the period of the Experiment lasting for one month. Group II was a group of rats which were given 189.0 parts per million of Mercury Chloride, which was the equivalent of 1.025 grams per 4.0 liters of distilled water. Group III was a series of rats which were fed 189.0 parts per million of Mercury Chloride in the drinking water, which was the equivalent of 1.025 grams per 4.0 liters of distilled water in combination with 63.0 parts per million of Zinc Chloride, which was the equivalent of 0.525 grams per 4.0 liters of distilled water. Group IV was a series of rats wherein only Zinc Chloride was included in the distilled water which was the equivalent of 0.525 grams per 4.0 liters of distilled water.

The amount of Mercury in each group of rats subsequent to sacrifice, was measured in both the hair and the liver/tissue of the rats. The measurement was provided at atomic absorption, cold-vapor, spectrophotometry methods well-known in laboratory use. The following results were found:

| Rat # No. | Trace Element Solution | Hair ng/L per 80 mg Dry Wt. | Liver-Tissue ng/L per 80 mg wet wt. |
|---|---|---|---|
| GROUP I | | | |
| 7 | 4-L Di H20 | 0.007 | 0.006 |
| 34m | | 0.010 | 0.006 |
| 33m | | 0.007 | 0.007 |
| 40 | | 0.004 | 0.010 |
| 41 | | 0.010 | 0.006 |
| 7m | | 0.006 | 0.003 |
| 33 | | 0.010 | 0.006 |
| 8m | | 0.014 | 0.006 |
| 15 | | 0.010 | 0.006 |
| 41m | | 0.005 | 0.006 |
| 14 | | 0.005 | 0.010 |
| | (average per group) | 0.008 | 0.007 |
| GROUP II | | | |
| 42m | 189 ppm | 0.030 | 0. |
| 42 | Mercury- | 0.098 | 0. |
| 8 | Chloride 2; | 0.076 | 0.312 |
| 9 | 1.025 g/ | 0.076 | 0.100 |
| 16 | 4-L Di H20 | 0.080 | 0.090 |
| 35 | | 0.030 | 0.042 |
| 41 | | 0. | 0.270 |
| | (average per group) | 0.065 | 0.163 |
| GROUP III | | | |
| 25m | 189 ppm | 0. | 0.065 |
| 11 | Mercury- | 0.055 | 0.132 |
| 11m | Chloride 2; | 0.058 | 0.145 |
| 36 | 1.025 g/ | 0.076 | 0.044 |
| 51 | 4-L Di H20, | 0.049 | 0.108 |
| 50 | 63 ppm Zinc- | 0.072 | 0.088 |
| 37 | Chloride 2; | 0.075 | 0.062 |
| 10 | 0.525 g/ 4-L Di H20 | 0.082 | 0.148 |
| | (average per group) | 0.067 | 0.100 |
| GROUP IV | | | |
| 52m | 63 ppm Zinc- | 0.024 | 0.025 |
| 13m | Chloride 2; | 0.020 | 0.014 |
| 37 | 0.525 g/ | 0.015 | 0.019 |
| 39 | 4-L Di H20 | 0.003 | 0.024 |
| 26m | | 0.030 | 0.016 |
| 12 | | 0.004 | 0.042 |
| 26 | | 0.004 | 0.007 |
| 13 | | 0. | 0.010 |
| 38 | | 0.009 | 0.014 |
| 12m | | 0.010 | 0.022 |
| 25 | | 0.020 | 0.045 |
| | (average per group) | 0.014 | 0.022 |

As can be seen, the amount of Mercury found in the hair between Groups II and III is substantially the same, however, the amount of Mercury found in the liver/tissue drops significantly from 0.163 ng per L per 80.0 mg of tissue to 0.100 ng per L per 80 mg. Thus, it is clearly shown that the amount of Mercury found in Group III was significantly less for the Mercury contained within the body of the sacrificed rats.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A nutrient compound having a predetermined plurality of elements being combined in an approximate weight percentage ratio each to the total of said elements within the approximate ranges including: (a) 0.032%–0.035% Scandium; (b) 11.090%–12.623% Titanium; (c) 0.247%–0.250% Vanadium; (d) 0.121%–0.141% Chromium; (e) 1.468%–1.689% Manganese; (f) 85.134%–86.455% Iron; (g) 0.030%–0.041% Cobalt; (h) 0.093%–0.106% Nickel; (i) 0.081%–0.085% Copper; and, (j) 0.120%–0.159% Zinc.

2. The nutrient compound as recited in claim 1 where each of said elements is in a composition form of an aqueous salt to form an aqueous nutrient solution.

3. The nutrient compound as recited in claim 2 where said total weight of said elements to said aqueous nutrient solution is within the approximate weight ratio of said elements of: 39,500 to 68,000 micrograms per 1.0 to 10.0 liters of said aqueous nutrient solution.

4. The nutrient compound as recited in claim 3 where said aqueous nutrient solution includes a pH value between the approximate range of 3.5–7.0.

5. The nutrient compound as recited in claim 3 including adding a predetermined quantity of Sodium Bicarbonate to said aqueous nutrient solution for varying a pH value of said aqueous solution to a predetermined value within the range approximating 3.5–7.0.

6. The nutrient compound as recited in claim 3 where said aqueous soluble salt of Scandium is in the form of Scandium Chloride.

7. The nutrient compound as recited in claim 3 where said aqueous soluble salt of Titanium is in the form of Titanium Chloride.

8. The nutrient compound as recited in claim 3 where said aqueous soluble salt of Vanadium is in the form of Ammonium Vanadate.

9. the nutrient compound as recited in claim 3 where said aqueous soluble salt of Chromium is in the form of Chromium Chloride.

10. The nutrient compound as recited in claim 3 where said aqueous soluble salt of Manganese is in the form of Manganese Chloride.

11. The nutrient compound as recited in claim 3 where said aqueous soluble salt of Iron is in the form of Iron Chloride.

* * * * *